(12) United States Patent
Eaton et al.

(10) Patent No.: US 11,090,463 B2
(45) Date of Patent: Aug. 17, 2021

(54) DEVICE WITH MEDUSA WIRE GROUP

(71) Applicant: Cook Medical Technologies LLC, Bloomington, IN (US)

(72) Inventors: Elizabeth A. Eaton, Bloomington, IN (US); Blayne Roeder, Bloomington, IN (US); Matthew Wildridge, Bloomington, IN (US); Joshua Sylvan, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 277 days.

(21) Appl. No.: 16/218,967

(22) Filed: Dec. 13, 2018

(65) Prior Publication Data

US 2020/0188637 A1 Jun. 18, 2020

(51) Int. Cl.
*A61M 25/01* (2006.01)
*A61F 2/24* (2006.01)

(52) U.S. Cl.
CPC ....... *A61M 25/0147* (2013.01); *A61F 2/2427* (2013.01); *A61M 25/0108* (2013.01)

(58) Field of Classification Search
None
See application file for complete search history.

(56) References Cited

U.S. PATENT DOCUMENTS

| | | | |
|---|---|---|---|
| 5,695,469 A | 12/1997 | Segal | |
| 5,944,712 A | 8/1999 | Frassica et al. | |
| 7,771,401 B2* | 8/2010 | Hekmat | A61M 25/0029 604/246 |
| 8,518,011 B2* | 8/2013 | Goodson, IV | A61M 25/0662 604/508 |
| 9,586,024 B2 | 3/2017 | Coates | |
| 2002/0042651 A1 | 4/2002 | Liddicoat et al. | |
| 2005/0101968 A1 | 5/2005 | Dadourian | |
| 2006/0069323 A1* | 3/2006 | Elkins | A61M 25/01 600/585 |
| 2006/0149350 A1* | 7/2006 | Patel | A61F 2/954 623/1.11 |
| 2011/0190708 A1* | 8/2011 | Shaked | A61F 2/954 604/180 |
| 2012/0265056 A1* | 10/2012 | Coates | A61M 25/0108 600/424 |

\* cited by examiner

*Primary Examiner* — Shaun L David
(74) *Attorney, Agent, or Firm* — Liell & McNeil

(57) ABSTRACT

A device includes a medusa wire group with at least three separate wires slidably received in a vascular catheter. The multiple wires of the medusa wire group maximize the chances of at least one wire entering a target branch vessel during an attempt to achieve access. Entry into the branch vessel may then be gained by advancing the vascular catheter over the at least one wire that successfully entered the branch passageway.

18 Claims, 7 Drawing Sheets

DEVICE WITH MEDUSA WIRE GROUP

TECHNICAL FIELD

The present disclosure is directed generally to a medical device, and more particularly to a "medusa" wire group used in combination with a vascular catheter to gain access to target branch vessels.

BACKGROUND

As endovascular aortic intervention patient demographics change, more and more devices are including fenestrations or branches, with more and more procedures necessitating significant catheter and wire manipulation to reach branch passages and access target branch vessels through fenestrations of stent grafts. Navigating from a stent graft lumen through a fenestration and into a target branch vessel often involves taking a sharp turn—for example a 90° turn into a renal artery. The renal-accessing or other vessel-accessing devices are being controlled at a remote proximal end outside of a patient's body by a physician, and the forces they exert on these devices are all being generated in planes potentially orthogonal to a target plane. Small motions at the user end need to be translated up the device, into the patient and result in the desired movement and orientation adjustments. This can be complicated by the potential movements of the stent graft fenestration and the target artery as well as anatomical variations and pathological conditions in vivo, as well as the generally two-dimensional grayscale view with an imperfect resolution of a complex three-dimensional space.

During a renal artery cannulation to place a stent across a fenestration in a fenestrated aortic stent graft, for example, the clinician manipulates a wire and vascular catheter through the fenestration and then through and into the renal artery. It is common to have the wire and/or catheter make it through the fenestration (potentially with the aid of preloaded components) only to spend a frustrating amount of time attempting to seek entry into the branch renal artery itself. Sometimes access to a target vessel is achieved with the wire or the catheter only to be subsequently lost. It is not unusual for the user to switch out vascular catheters over the wire multiple times when they are having difficulty, trying different shapes and subtly influencing them by advancing and pulling back the wire to gain access to the renal artery. Similar problems abound for other branch passage access issues with or without the involvement of fenestrated stent grafts.

The present disclosure is directed toward one or more of the problems set forth above.

SUMMARY

In one aspect, a device includes a vascular catheter terminates at a distal end that defines a seeking direction. A medusa wire group that includes at least three separate wires is slidably received in the vascular catheter. The device has a maneuvering configuration in which a distal end of each of the wires is completely positioned inside the vascular catheter. The device has a seeking configuration in which a distal segment of each of the separate wires is spaced from the distal end of the vascular catheter and freely movable with respect to each other. A distal end direction defined by each of the separate wires is at an acute angle with respect to the seeking direction. The device also has an access configuration in which the distal end segment of at least one of the separate wires is positioned within a cylindrically shaped target volume that is outside of the vascular catheter and intersected by a line coincident with the seeking direction.

In another aspect, a method of accessing a branch passageway from a main passageway with a device includes positioning a vascular catheter of the device in the main passageway so that a seeking direction defined by a distal end of the vascular catheter points into the branch passageway. A medusa wire group of the device is simultaneously slid within the vascular catheter to a seeking configuration in which a distal segment of each of the separate wires of the medusa wire group is spaced from the distal end of the vascular catheter, and a distal end direction defined by each of the separate wires is at an acute angle with respect to the seeking direction. The device is changed to an access configuration in which the distal end segment of at least one of the separate wires is positioned within the branch passageway.

DETAILED DESCRIPTION

Figure 1:
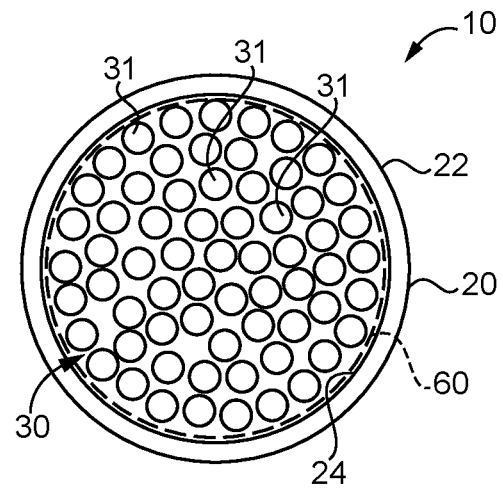
FIG. 1 is a distal end view of a device according to the present disclosure.

The present disclosure concerns a wire guide distal segment comprised of multiple individual wire sections that is referred to herein as a medusa wire group. The purpose of the individual wires is to maximize the chances of at least one of the wires successfully entering a target vessel, such as a renal artery during a given advancement. The user may bring the medusa wire group into position near a target vessel with a vascular catheter, and then attempt to advance into the target vessel in a normal known manner. Some, maybe many and potentially most, of the individual wires of the medusa wire group will encounter resistance upon hitting a main vessel wall, such as the aorta, and buckle or misdirect. Other wires of the medusa wire group, potentially as few as one of the wire segments will successfully pass through the target vessel ostium. Thereafter, the vascular catheter may be advanced along the successful wire(s) and enter the target vessel while dragging the misdirected wires along. The medusa wire group may then be exchanged with a more traditional wire, such as a standard 0.038 inch wire guide, before further treatment in the particular case proceeds.

Several possibly cross-coupled variables may need to be considered when arriving at a medusa wire group suitable for use in a particular application. As used in this disclosure, a medusa wire group always includes at least three separate wires. A vascular catheter according to the present disclosure means a catheter intended for use in the vascular system, as opposed to catheters for other systems, such as genitourinary catheters. Some vascular catheters according to this disclosure may be used with a seeking wire guide such that the catheter includes a curved pre-formed distal end segment that terminates in a distal end that defines a seeking direction. Other vascular catheters used in angiographic, diagnostic, flushing and other vascular procedures are also considered vascular catheters within the scope of this disclosure.

One variable, namely the diameter of the individual wires of the medusa wire group may lead to even further subvariables. In order to increase the number of wires of the medusa wire group, and in consideration of various factors including maneuverability/torque control, vessel diameter, sheath diameter, and catheter diameter among others, it may be desirable to minimize the diameter of the individual wires. Reducing diameter, with all other factors being held equal, may also reduce column strength. There ought to be a balance between sufficient column strength so that the medusa wire group may be advance toward a target vessel while maintaining a forward orientation associated with a seeking direction of a vascular catheter in the face of blood flow, but have sufficient column weakness to encourage collapse or even perhaps breakage (where desired) of the unsuccessful wires of the medusa group. "Unsuccessful" means those wires that do not enter the target vessel ostium, but instead buckle or are otherwise misdirected. The number of discrete wires in the medusa wire group can alter the probability of at least one of the wires successfully entering the target vessel ostium. As few as three wires could potentially triple the chances of a successful outcome while reducing an overall diameter, complexity and potential drag upon successful advancement. Circular cross-sectional packing suggests that, for example, four wires of 0.014 inch diameter will fit in the same space as a single 0.038 inch wire, while as many as sixteen wires of 0.008 inches will fit in the same space as a single 0.038 inch diameter wire that is often the diameter of choice for physicians performing aortic, renal, mesenteric or other interventions. The cross-sectional geometry of the individual wires of the medusa wire group may also contribute to a successful outcome. While wire guides are traditionally circular in cross section in order to eliminate orientation bias and maximize the utility of torque transmission, the individual wires of the medusa wire group need not be universally circular in cross section or respond identically to torques initiated in the proximal end of the medusa wire group by the clinician. Because an orientation of the individual wires could be fixed relative to each other, the non-circular and/or varying wiring cross sectional shapes might serve to enhance the functional possibilities of additional wires of the medusa wire group successfully entering a vessel ostium. The material out of which the medusa wire group is formed, in conjunction with diameter, could play a large role in column strength of the individual wires. Additionally, utilizing multiple wires of varying column strength flex moduli, and other material characteristics in one medusa wire group would increase diversity of behavior in response to a user stimulus which could further increase the likelihood of a successful outcome in entering a difficult access branch vessel. Considering wires for the medusa wire group that reduce the likelihood of breakage or other undesirable events may promote consideration of harm reduction materials, such as magnesium that will dissolve in a patients body, that can also be implemented to further drive down adverse risks. However, frangibility could be intentionally selected as an alternative variable as part of a desired treatment outcome. Thus, some or all of the wires 30 could be manufactured from a bioresorbable material, such as including magnesium, that would break instead of bending backwards in the event that that particular wire was misdirected. In such a case, the broken tips of the misdirected wires would gradually dissolve, rather than being dragged into the target vessel as the catheter is advanced over the wire(s) that properly enter the target vessel ostium. Wires made with bioresorbable material like magnesium could be designed to have enough column strength to drive forward against flow but insufficient column strength to bend backwards when faced with collision with a solid material (e.g., tissue, graft material, stent strut, etc.). When the medusa wire head is advanced, the wires that make it into the target vessel without contact with other structures would remain intact, while those that hit something along the way would just fracture, and leave small filaments to drift downstream and dissolve in place or further downstream over time. The pre-formed relative configuration of the wires in the medusa wire group, if any, along with trade-offs in the above-described features, individual patient anatomy, and diverse arterial target conditions may favor certain configurations over others. Four different example configurations, different from shared parallelism, are shown for example in FIG. 16.

After one or more of the individual wires of the medusa wire group successfully enter the target vessel ostium, some capture mechanism must typically then be used in order to proceed further with a given intervention. Those skilled in the art will appreciate that the simplest capture mechanism will work by advancing the vascular catheter or other accessory device over the medusa group in order to exchange the medusa wire group for a traditional wire guide. More complicated capture mechanisms could potentially eliminate the exchange step in at least some procedures. Such mechanisms might include a co-axial wire design, which is essential built-in accessory sheath for the wire, or the use of induced magnetism to turn the wire into a solenoid in passing an electrical current along its length via a hook up outside of the patients body to realign and hold together the wires of the medusa group briefly or semi-permanently to adjust a recapturing top cap at the far distal end of the medusa wire group.

Figure 2:
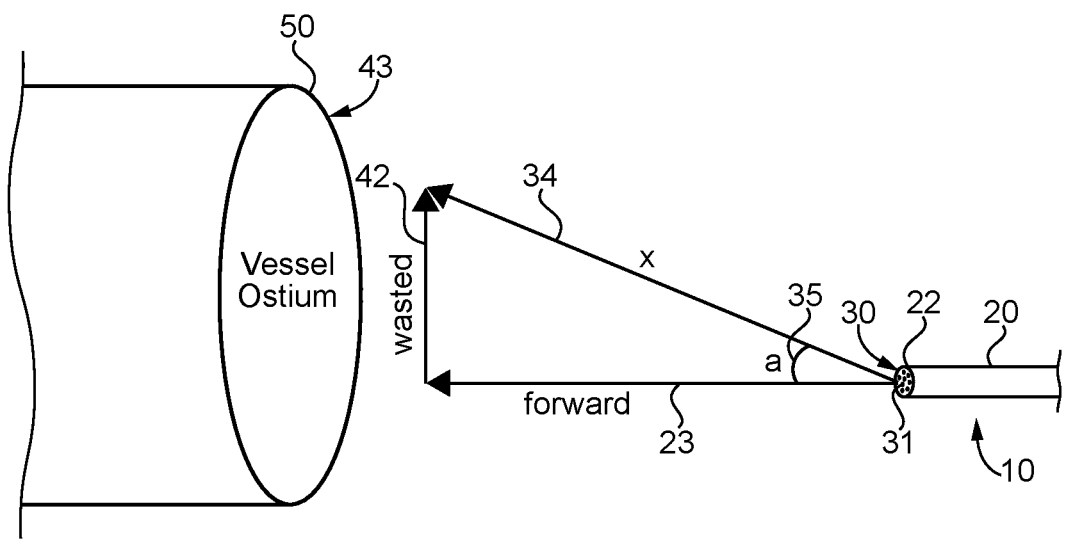
FIG. 2 is a geometric sketch illustrating the geometry of accessing a branch vessel ostium.

Referring initially to FIG. 1, a device 10 according to the present disclosure includes a vascular catheter 20 that defines a lumen 24 and has a distal end 22. A medusa wire group 30 includes at least three separate wires 31 slidably received in the vascular catheter 20. Referring now in addition to FIG. 2, the geometrical considerations associated with the device 10 are illustrated. The distal end 22 of the vascular catheter 20 defines a seeking direction 23, which is illustrated as pointing in the direction of a target vessel ostium 43, such that the target vessel defines a cylindrically shaped target volume 50. Before being advanced distally out of the distal end 22 of vascular catheter 20, the individual wires 31 of the medusa wire group 30 may be generally parallel, especially if the number of wires substantially fills lumen 24 of catheter 20. As such, the wires 31 may all initially point in the seeking direction 23 defined by the distal end 22 of catheter 20. However, upon emerging from distal end 22, the individual wires may stray from the seeking direction 23 such that each individual wire can be thought of as defining a distal end direction 34 that will initially be at an acute angle 35 with regard to seeking direction 23. As used in this disclosure, zero is an acute angle. Straying may occur passively in response to some external stimulus or be responsive to material geometry and/or device properties, such as by use of shape memory materials. As illustrated, the distal end direction 34 will include a component parallel to the seeking direction 23, and an off-axis direction component 42. Some or all of the individual wires 31 may include some feature, such as being metallic or including a marker, that enables appropriate imaging to determine the whereabouts of each wire 31 during an accessing procedure. Nevertheless, those skilled in the art will appreciate that factors like a high number of wires, low-visibility material in the wires, thin wire geometry, high patient mass, low radiation or poor-kidney-function-driven requirements, etc. may complicate this. In these cases, the visibility of the (shape of) the group of wires could be sufficient. You may not necessarily need to individually differentiate each and every wire in order to access a target vessel with the device of the present disclosure.

Assuming the individual wires 31 originate from a common catheter 20 and point in any one of several different directions, each individual wire 31 may be considered to contribute a force vector in its individual distal end direction 34, which may differ from the seeking direction 23 by the initially acute angle 35. Together, the wires 31 can define a net force direction having a magnitude component along the seeking direction 23 and a net magnitude component in an orthogonal or off axis direction that is a vector sum of the distal end direction 34 of the wires 31. Trigonometry dictates that as the angle 35 decreases, the magnitude of a net force acting in the seeking direction 23 increases, and a magnitude of a wasted force vector in an orthogonal off-direction decreases. Because the off axis component of different wires 31 may cancel each other in contributing to a net force direction of the medusa wire group 30, the contribution of each wire 31 to the overall medusa group is not simply 1/n, but some fraction thereof, with wires 31 pointing more closely in the desired seeking direction 23 contributing more motive force in that direction than wires pointing less closely to the desired seeking direction 23. In fact, a "spray" of wires 31 or other assortment, the contributions of the off axis components may not only be minimized for a given wire but cancelled out, in part or in whole depending on several factors. This by itself might be unremarkable if the direction of motion of the medusa wire group 30 originating from the distal end 22 of catheter 20 was perfectly controlled via steerability control of the vascular catheter 20 and with possible precision with appropriate imaging. Since it is not, the direction of motion of the medusa wire group is likely to be generally close to the desired seeking direction 23. As long as the medusa wire group is closer to this desired direction than not, the presence of at least three wires 31 acts to tip the scales in favor of both accessing the target vessel ostium, and maybe more importantly being able to communicate the majority of force applied in that direction once the target vessel has been found.

Some analysis suggests two design considerations. First, the size of the "spray" or brush head defined by the wires 31 of the medusa wire group may be tailored to be within some multiple of the target vessel ostium size for improved outcomes. In addition, failure may still be possible with the device 10 of the present disclosure especially when the overall positioning of the vascular catheter 20 and the medusa wire group is not pointing toward the vessel ostium. Thus, the present disclosure does not guarantee access to a target vessel ostium, but may greatly increase the likelihood of successfully achieving a target.

Figure 5:
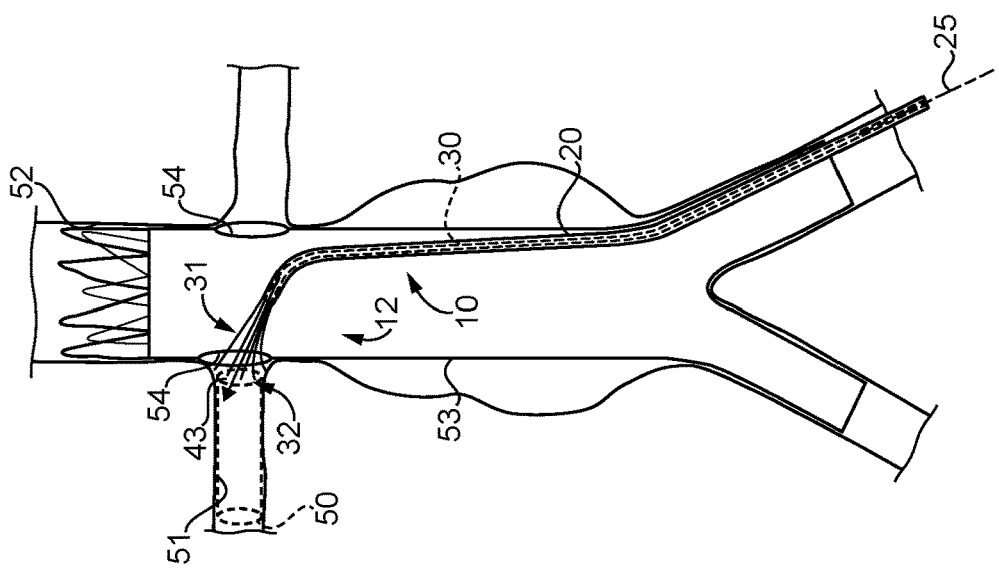
FIG. 5 is a schematic view similar to FIG. 4 also showing the device later in the procedure but still in the seeking configuration.
Figure 4:
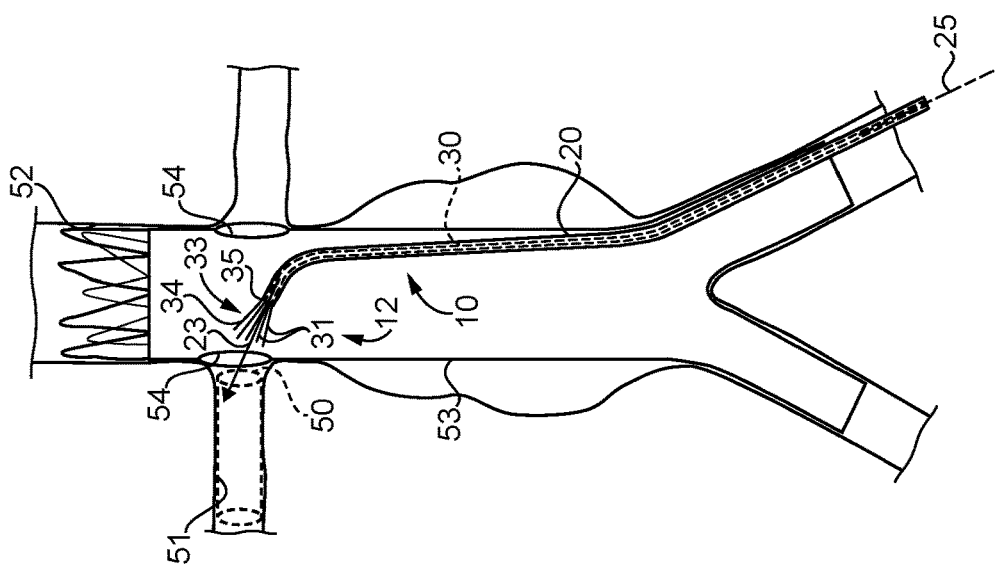
FIG. 4 is a schematic view similar to FIG. 3 showing the device in a seeking configuration.
Figure 3:
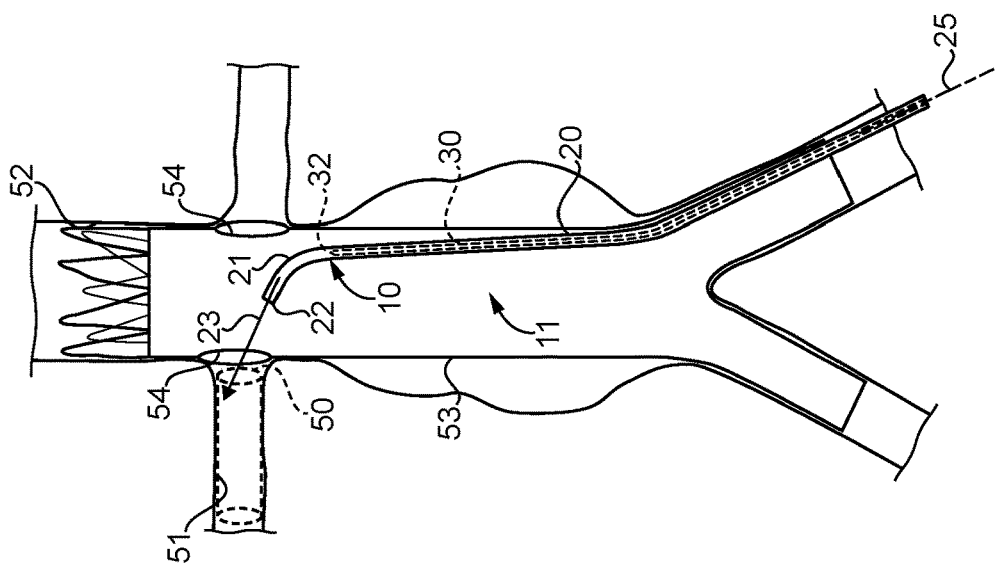
FIG. 3 shows a schematic view of an aortic intervention procedure while accessing a renal artery through a fenestration of a stent graft according to the present disclosure, showing the device in a maneuvering configuration.
Figure 6:
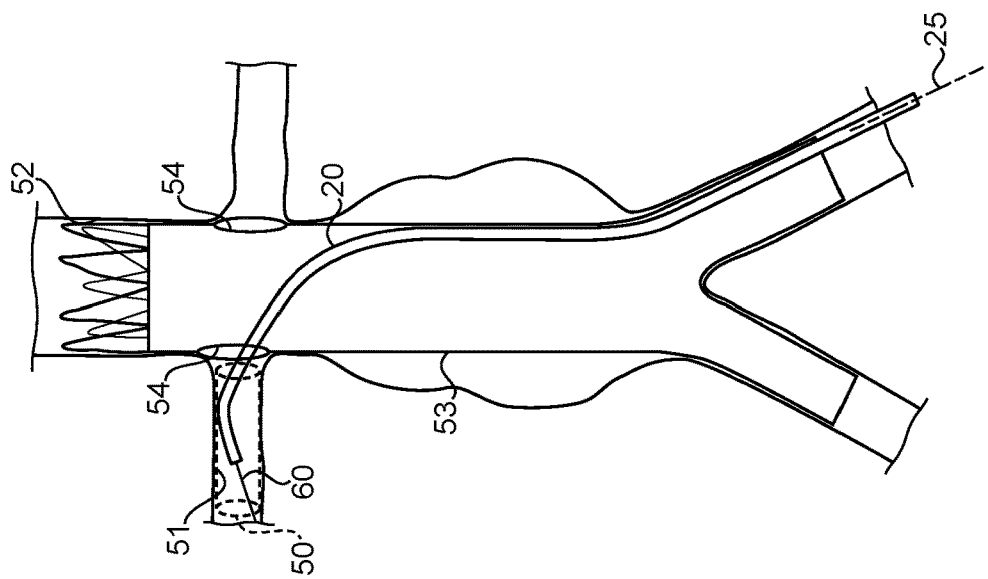
FIG. 6 is a schematic view similar to FIG. 5 showing the device in an accessing configuration.
Figure 7:
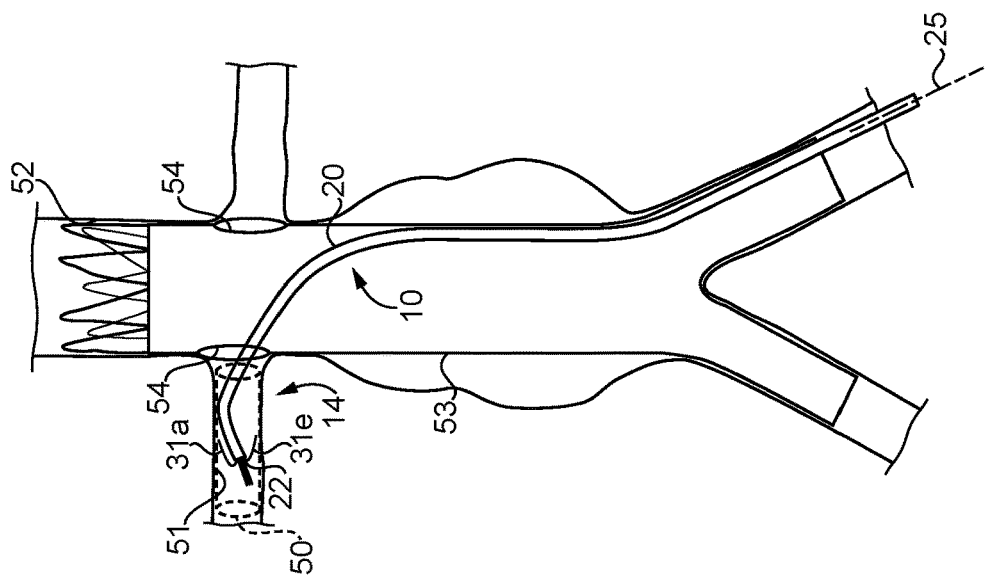
FIG. 7 is a schematic view similar to FIG. 6 showing the device in an entered configuration.
Figure 8:
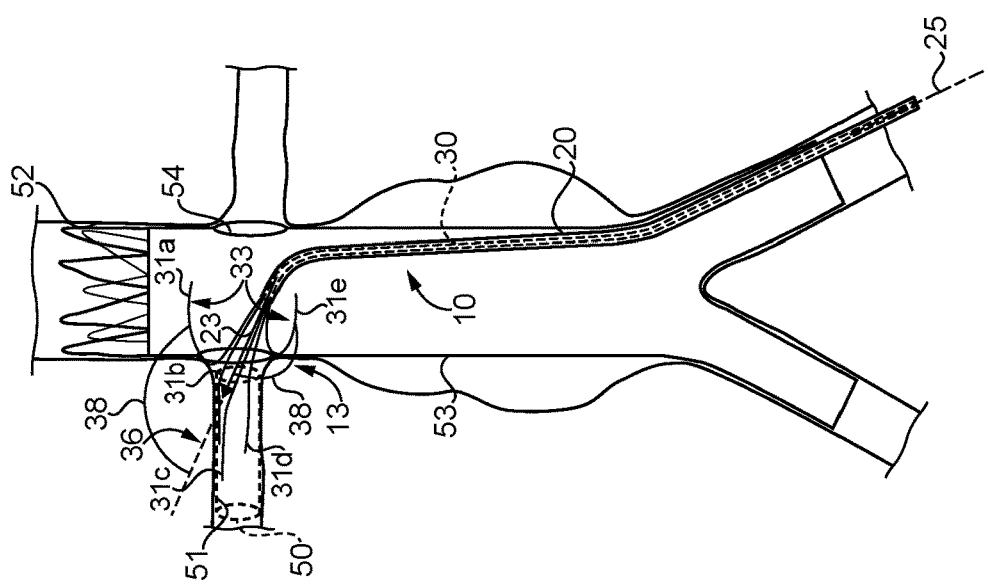
FIG. 8 is a schematic view similar to that of FIG. 7 after the medusa wire group has been exchanged with a typical 0.038 inch wire guide.

Referring now to FIGS. 2-8, the device 10 is illustrated in the context of seeking access to a renal artery 51 through a fenestration 54 defined by a stent graft 53 positioned for treatment of an aneurysm in aorta 52. Although the figures show the renal artery 51 being approached from below, procedures approaching from above the would also fall within the intended scope of this disclosure. In FIG. 3, device 10 is shown in a maneuvering configuration 11 in which the distal ends 32 of each of the separate wires 31 of the medusa wire group 30 are positioned completely inside vascular catheter 20. Those skilled in the art will appreciate that the individual wires 31 may extend the full length of catheter 20, or may have their proximal ends attached to a common push wire that may form the majority of a length of the medusa wire group 30. Prior to proceeding, the physician may position and orient the vascular catheter 20 either at or through the fenestration 54 so that the seeking direction 23 defined by the distal end 22 of the catheter 20 points through the fenestration 54 and into the target vessel, which in this case is the renal artery 51. FIG. 4 shows device 10 being changed to a seeking configuration 12 in which a distal segment 33 of each of the separate wires 31 of medusa wire group 30 is spaced from the distal end 22 of vascular catheter 20 and freely movable with respect to each other in the presence of continued blood flow through the aorta heading into the renal and other outlets including down to the iliac arteries. The seeking configuration 12 is also characterized by the distal end direction 34 defined by each of the separate wires 31 at an acute angle 35 with respect to the seeking direction 23. In this sequence of illustrations, the medusa wire group 30 is shown as including five individual wires 31. The number of wires 31 could, however, be as few as three, or many more than five as shown for example in FIG. 1. FIG. 5 shows the wires 31 further advanced still in the seeking configuration 12 with several of the wires approaching the target vessel ostium 43. FIG. 6 shows the device 10 in an access configuration 13 in which the distal end segment 33 of at least one, in this case three of five of the separate wires 31 is positioned within a cylindrically shaped target volume 50, which is defined by the target vessel. It should be noted that the approximately cylindrically shaped target volume 50 will always be located outside of the vascular catheter 20, and should be intersected by a line coincident with the seeking direction 23. FIG. 6 is also of interest for showing that one of the wires 31a encounters an obstacle and is redirected in an opposite direction away from target vessel 51. In this example wires 35b, c and d successfully access renal artery 51 and are positioned in the cylindrically shaped target volume 50. The fifth wire, 31e apparently encountered an obstacle and was turned backward away from the target vessel. Thus, in this example, three of the five wires successfully entered the target vessel, and one could expect the off-axis components of the two errant wires 31a and 31b to substantially cancel each other out so that the vascular catheter 20 could be expected to follow the other three wires (31b, c and d) into the renal artery 51, dragging the bent unsuccessful wires with it. FIG. 7 shows device 10 in an entered configuration 14 in which the distal end 22 of the vascular catheter 20 is positioned within the cylindrically shaped target volume 50. This was accomplished by advancing vascular catheter 20 in a distal direction over the medusa wire group. As can be seen, the wires 31 are designed to be sufficiently flexible that they move along a rolling bend as the catheter 20 is advanced into the branch artery. Thus, wires 31a and 31e can be considered to be bent about and in contact with the distal end 22 of catheter 20. FIG. 8 shows the procedure after the medusa wire group 30 has been withdrawn from vascular catheter 20 and exchanged with a standard wire guide, such as a 0.038 inch wire guide 60 of the type preferred by many cardiovascular surgeons for procedures in this vascular bed.

In the example of FIGS. 2-8, the individual separate wires 31 of the medusa wire group 30 are fixed against relative movement along axis 25 of vascular catheter 20 when the wires are within vascular catheter 20. As shown in FIG. 6, when device 10 is in access configuration 13, a majority 36 of the distal end directions defined by the individual wires 31b, c and d are at an acute angle with respect to the seeking direction 23, while a minority 37 (wires 31a and 31e) of the distal end directions defined by those respective wires are at an obtuse angle 38 with respect to the seeking direction 33. This relationship may further persist into the entered configuration 14 shown in FIG. 7. Both FIGS. 6 and 7 illustrate that the distal end direction defined by some of the wires, namely 31a and 31e are at an obtuse angle 38 with respect to the seeking direction 23.

Figure 10:
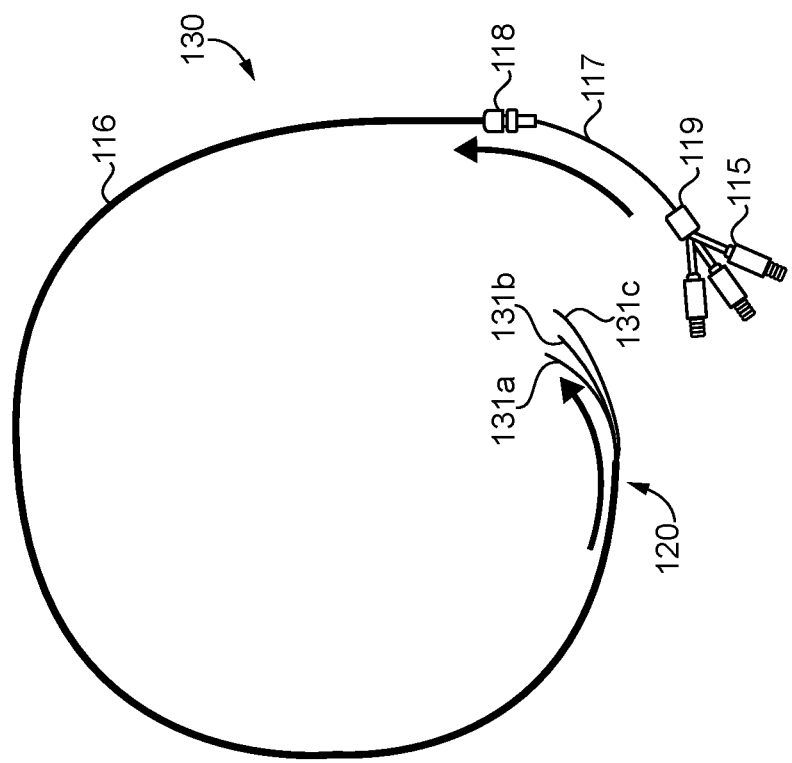
FIG. 10 is a schematic view of the device of FIG. 9 showing manipulation of the device to expose the wires of the medusa wire group.
Figure 9:
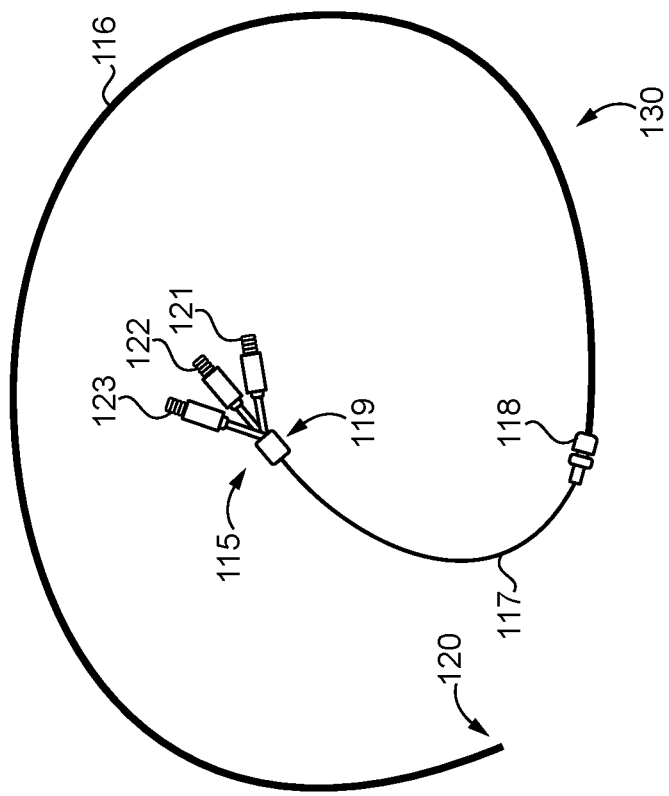
FIG. 9 is a schematic view of a device according to another embodiment of the present disclosure.
Figure 11:
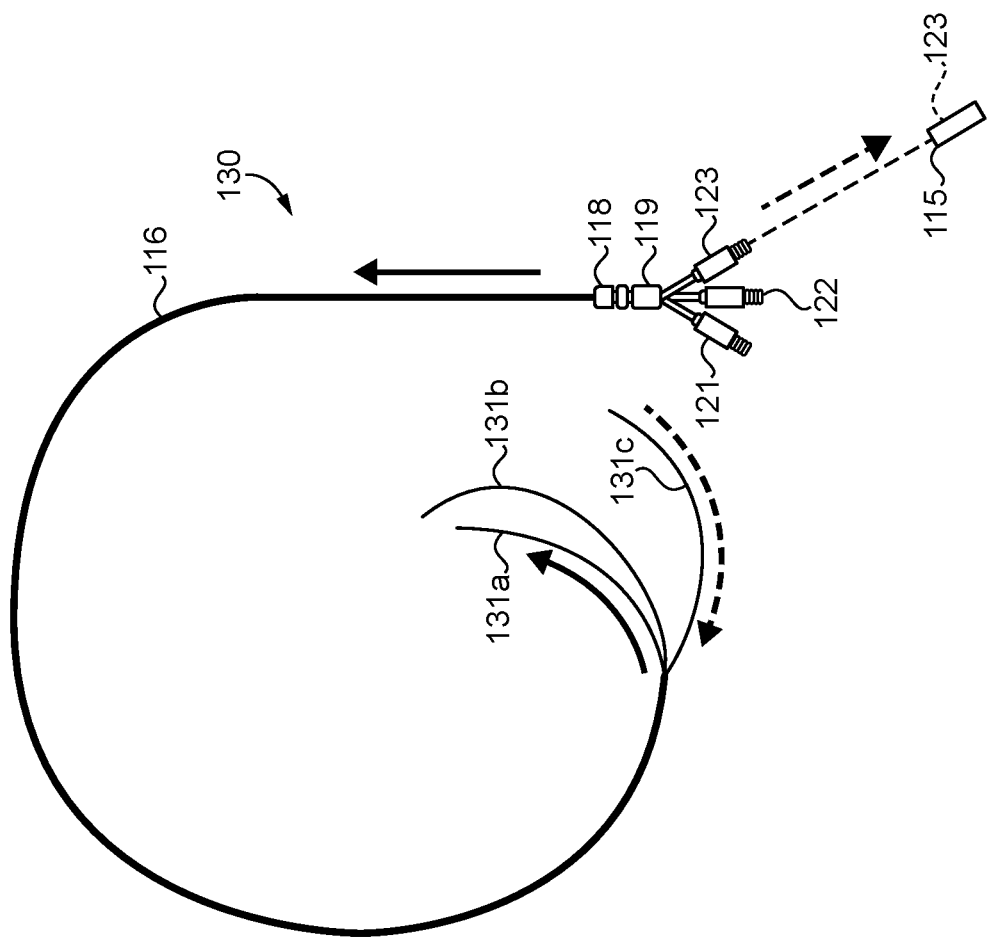
FIG. 11 is a schematic view similar to FIG. 10 with the separate wires of the medusa group fully exposed and illustrating how the wires can be individually withdrawn.

Referring now to FIGS. 9-11, a medusa wire group 130 according to another embodiment of the present disclosure is illustrated. Medusa wire group 130 differs from the earlier described medusa wire group 30 in that the individual wires, three in this example embodiment, may be slid with respect to each other along an axis defined by wire containment catheter 116, whereas the medusa wire group 30 described earlier in the individual wires 31 were fixed against sliding relative to one another along an axis 25 of the vascular catheter 20. Nevertheless, the wires 31 of the previous embodiment could be made to be slidable relative to one another without departing from the intended scope of the present disclosure. Medusa wire group 130 includes three wires 131 that are attached at proximal ends 115 to respective first handle 121, second handle 122 and third handle 123. Handles 121-123 move with respect to a base hub 119, which is attached to a slide catheter 117 that is received in containment catheter 116. When base hub 119 is moved with handles 121-123 toward a stop hub 118 affixed to containment catheter 116, the individual wires 131 emerge from a distal end of containment catheter 116 as shown in FIG. 11. At this point, the individual handles, such as handle 123, may be moved away from base hub 119 to withdraw the individual wire 131 that is attached to the respective handle 123. Thus, in this embodiment, the individual wires 131 are slidable with respect to each other along an axis of the vascular catheter when positioned within a vascular catheter.

Figure 12:
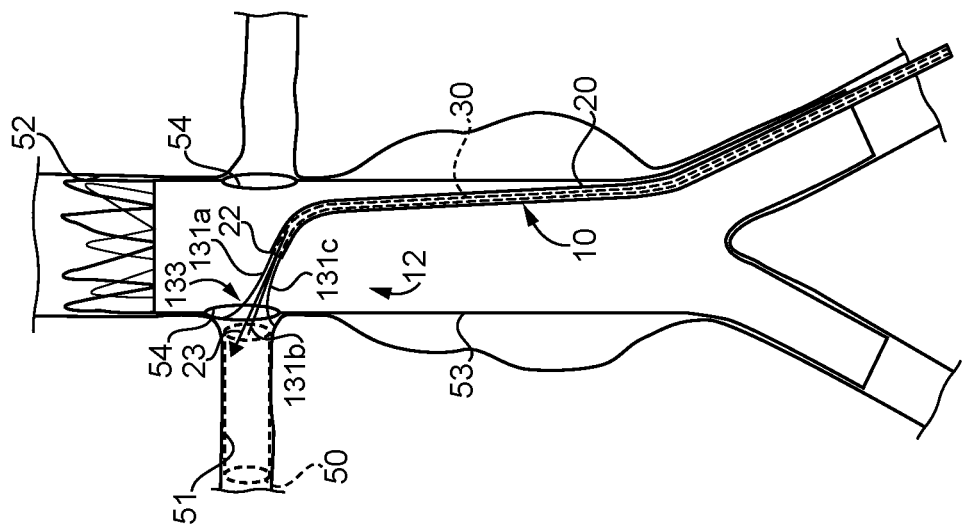
FIG. 12 is a schematic view of an aortic intervention with the device of FIGS. 9-11 in a seeking configuration attempting to access a renal artery through a stent graft fenestration.
Figure 13:
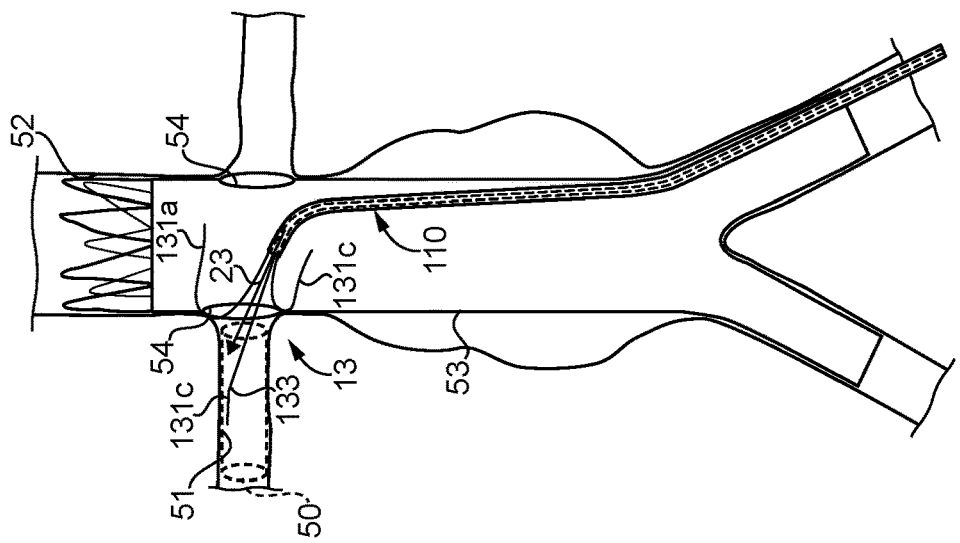
FIG. 13 is a view similar to FIG. 12 showing the device in an access configuration.
Figure 14:
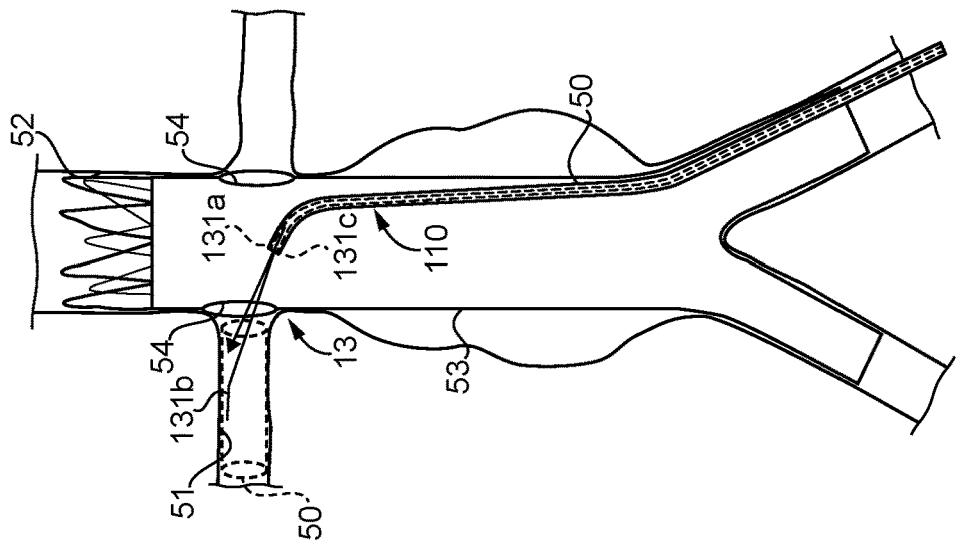
FIG. 14 is a schematic view similar to FIG. 13 in an access configuration.
Figure 15:
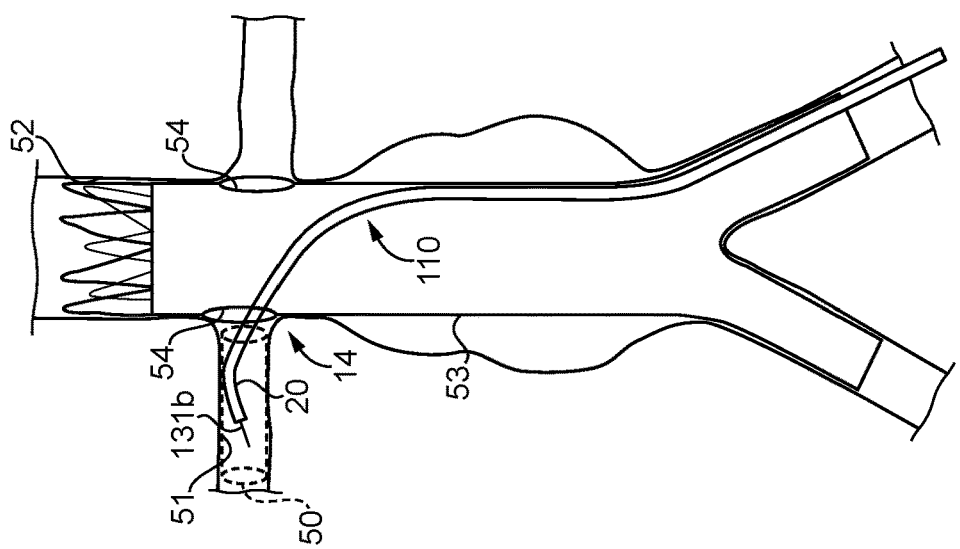
FIG. 15 is a schematic view similar to FIG. 14 except showing the device after achieving the entered configuration into the renal artery.

Referring now to FIGS. 12-15, the medusa wire group 130 of FIGS. 9-11 is shown in use with the vascular catheter 20 described earlier. FIG. 12 shows device 110 in the seeking configuration 12 in which the distal segment 133 of each of the separate wires 131 is spaced from the distal end 22 of vascular catheter 20 and are freely movable with respect to each other. In addition, a distal end direction defined by each of the separate wires 131 is at an acute angle with respect to seeking direction 23. FIG. 13 shows device 110 in the in the access configuration 113 in which the distal end segment 133 of wire 131b is positioned within cylindrically shaped target volume 50. In this example, the other two wires 131a and 131c encounter obstacles and turn back or away from the target vessel forming obtuse angles with regard to seeking direction 23. FIG. 14 shows device 110 later in an access configuration 13 in which the two errant wires 131a and 131c have been withdrawn back into vascular catheter 20 responsive to proximal movement of their respective handles 121 and 123 (FIGS. 9-11) so that only the successful wire 131b is left in the cylindrically shaped target volume 50. FIG. 15 shows device 110 in the entered configuration 14 of which the distal end 22 of vascular catheter 20 has been advanced successfully along medusa wire group 130 so as to be positioned within cylindrically shaped target volume 50. Thereafter, the medusa wire group 130 may be exchanged with a conventional standard wire so that the procedure may continue, such as with the implantation of a branch stent graft in renal artery 51 through fenestration 54.

Figure 16:
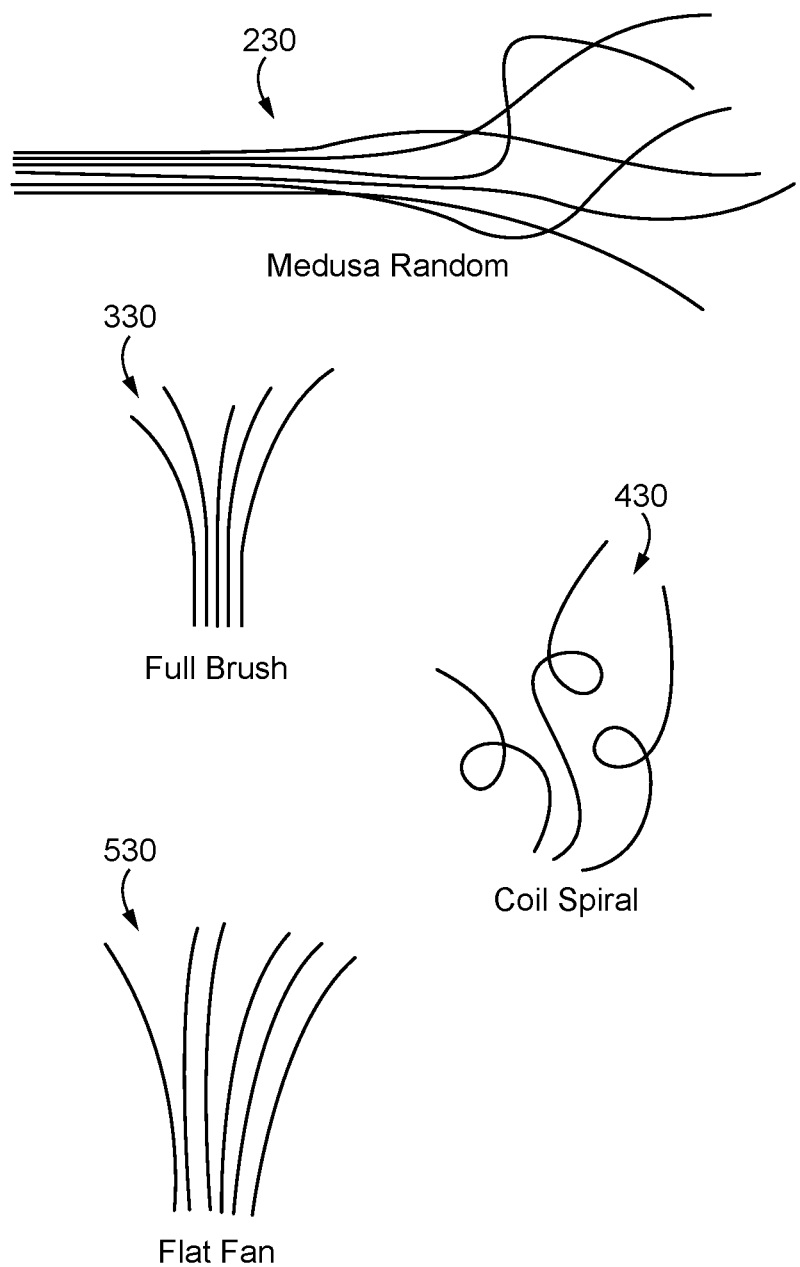
FIG. 16 is a schematic view of different medusa wire group configurations according to the present disclosure.

Referring now to FIG. 16, several different medusa wire groups that would fall within the scope of the present disclosure are illustrated. While the previous embodiments could represent narrow versions of a full brush 330 having a conical spread verses a flat fan 530 in which the individual wires are spread in a common plane. The earlier illustration showed situations in which the individual wires are not preformed with any shape and are all parallel with one another. The present disclosure also contemplates the individual wires having different preformed end shapes such as a random collection 230 as shown or the individual wires could be coiled in spirals as 430. Thus, any combination of preform or lack thereof in the individual wires that make up the medusa wire group would fall within the intended scope of the present disclosure.

INDUSTRIAL APPLICABILITY

The present disclosure finds application where there is a need to access a branch passageway from a main passageway in a patient. While this general applicability may be mainly for cardiovascular interventions, and maybe more important on the arterial side, the present disclosure could also apply to non-blood related body passageways having branch passages needing to be accessed. The present disclosure finds particular application in accessing branch passageways from main passageways, such as a branch artery from the aorta. The present disclosure finds specific application in accessing branch passageways through fenestrations of stent grafts, especially in relation to aortic interventions, such as a fenestrated stent graft for aortic aneurysm repair.

When in use, a clinician will typically prepare a patient and insert a fenestrated graft 53 over a wire such that the delivery system is in place inside the patient's aorta with the location approximately where the stent graft 53 is desired to be implanted. The clinician then may start deployment such that a portion of the graft, which includes fenestrations 54. The fenestration should roughly line up with the target vessel, such as renal artery 51, ostium 43. Pre-loaded wires (not shown) inside the graft 53 may traverse the fenestration inside to outside. The clinician may then take a vascular catheter 20, maybe with one of a variety of specialized distal end segment curves known in the art for accessing target vessel up over the preloaded wire such that the catheter now rests inside the graft 53 with its distal end defining a seeking direction 23 pointing at or through the fenestration 54 in the graft 53. The clinician can then remove the preloaded wire (not shown). Next, the clinician may insert the medusa wire group 30, 130 through the vascular catheter 20 in the maneuvering configuration in which the distal ends of each of the separate wires 31, 131 is completely positioned in the vascular catheter 20 as shown for example in FIG. 3. Thus, the vascular catheter 20 of the device 10, 110 may be considered to be positioned in a main passageway, such as the aorta, so that the seeking direction 23 defined by the distal end 22 of the vascular catheter 20 points towards the branch passageway, which in this case is the renal artery 51. Next, the clinician simultaneously slides the medusa wire group 30, 130 to a seeking configuration within the vascular catheter to a seeking configuration 12 in which the distal end segment of each of the separate wires 31, 131 is spaced from the distal end 22 of vascular catheter 20 and a distal end direction defined by each of the separate wires 31, 131 is at an acute angle, which could be zero degrees, with respect to the seeking direction 23 as shown in FIGS. 4 and 12. Next, the device 10, 110 is changed to an access configuration 13 in which the distal end segment of at least one of the separate wires 31, 131 is positioned within the branch passageway 51 as shown in FIGS. 6, 13 and 14. Thus, from the many stranded version of the medusa wire group 30, the physician advances the medusa wire group 30 toward the target until all of the wires have made it sufficiently deep into the target vessel 51 or have gone astray and are bent backward away from the target vessel. When the successful wires go deep enough in that the remaining wires can be easily assimilated by the action of the advancing catheter 20, the catheter will tend to follow the successful wires to an entered configuration 14 with the distal end 22 of the catheter positioned in the target branch vessel 51 as shown in FIG. 7. In the case of the device of 110, the clinician may advance all of the wires toward the target vessel, and then retract those unsuccessful wires leaving only that subset of wires that successfully entered the target branch vessel to guide vascular catheter 20 into the entered configuration as shown in FIG. 15. Thereafter, the clinician withdraws the medusa wire group 30, 130 and may exchange with a standard wire guide, such as a 0.038 inch wire guide of the type preferred by many clinicians performing aortic interventions, and then the procedure advances as per usual.

Those skilled in the art will appreciate that because the unsuccessful wires can often cancel each other out as far as their off-axis directions, the distal end 22 of the vascular catheter 20 when being advanced may be considered to move along a net wire direction that may be approximated by an average vector sum of all the distal end directions of all of the wires 31 of the medusa wire group 30. As best shown in FIGS. 6 and 7, when the catheter 20 is advanced, the unsuccessful wires may bend about and be in contact with the distal end 22 of vascular catheter 20. In fact, the unsuccessful wires may be bent back at an obtuse angle with regard to the seeking direction 23. In the specific examples shown, the successful wire extends from catheter 20 within graft 53, which is positioned within the main passageway of the aorta, and through fenestration 54 into the branch passageway, which is in this case the renal artery 51.

One advantage of the medusa wire group 30, 130 of the present disclosure is potential time savings during complex aortic intervention procedures, and the reduction in variation between requirements among different patients. In other words, the medusa wire group of the present disclosure may reduce the skill level necessary to gain access to branch passageways during these procedures. Essentially, one could expect the medusa wire group in particular and the device 10, 110 specifically to work similarly and within a similar time frame regardless of the angle of take off of a target artery, and even in the presence of thrombus or calcification, vessel tortuosity, or other potential complications.

Another advantage of the present disclosure is the non-specificity of manipulation required in using the medusa wire group. Since manipulations originate outside the patient at the proximal end of wire type devices, it can be challenging to fine-tune which actions are needed by the clinician to result in the same end result, depending upon all of the intervening variations. The medusa wire group design requires relatively non-specific behavior by the clinician by relying on a large number of partially independent distal contact points defined by the individual wires 31, 131 of the medusa wire group 30, 130. One rotation at the proximal end will effect each end point differently, and the aggregate mass of contact points will be much more likely to have one successful result of at least one of the wires entering the target vessel.

A third advantage of this design can be that concomitant haptic feedback during use of the medusa wire group may obviate the use of contrast during this portion of an aortic intervention procedure. For patients with poor GFR or who otherwise cannot tolerate contrast, reduction in the contrast use can be a significant advantage. By relying upon haptic feedback and the natural behavior of the wire, the clinician may also reduce the use of fluroscopic imaging, and the resulting radiation exposure for both the patient and the others present for the procedure. Thus, the present disclosure has the potential benefit of reducing radiation dosages and/or time exposure to radiation, reduce anesthesia doses and/or time, reduce procedural time and possibly cost, and potentially reduce procedure complexity. Finally, the present disclosure has the potential to incrementally improve procedural success rate, and increase applicability of various vascular therapies to a wider demographic than that practically possible with previously known strategies.

The following invention definitions are not claims but could be used to support multiple dependency type claims often favored in Europe. 1. A medical device includes a vascular catheter that terminates at a distal end that defines a seeking direction; a medusa wire group that includes at least three separate wires slidably received in the vascular catheter; the device having a maneuvering configuration in which a distal end of each of the separate wires is completely positioned inside the vascular catheter; the device having a seeking configuration in which a distal segment of each of the separate wires is spaced from the distal end of the vascular catheter and freely movable with respect to each other, and a distal end direction defined be each of the separate wires being at an acute angle with respect the seeking direction; and the device having an access configuration in which the distal end segment of at least one of the separate wires is positioned within a cylindrically shaped target volume that is outside of the vascular catheter and intersected by a line coincident with the seeking direction. 2. The device of definition 1 wherein the separate wires are fixed against relative movement along an axis of the vascular catheter and within the vascular catheter. 3. The device of any of definitions 1 or 2 wherein the separate wires are slidable with respect to each other along the axis of the guide catheter and within the vascular catheter. 4. The device of any of definitions 1-3 wherein the access configuration includes a majority of the distal end directions being at an acute angle with respect to an average distal end direction of the majority, and a minority of the distal end directions are at an obtuse angle with respect to the seeking direction. 5. The device of any of definitions 1-4 wherein the access configuration includes a distal end of at least one of the separate wires positioned inside the vascular catheter. 6. The device of any of definitions 1-5 wherein the medusa wire group has a cross-sectional area less than a cross-sectional area of a 0.038 inch wire guide. 7. The device of any of definitions 1-6 wherein the access configuration includes at least one of the separate wires is bent about and in contact with the distal end of the vascular catheter. 8. The device of any of definitions 1-7 wherein the distal end direction of each of the at least one wires bent about the distal end of the vascular catheter is at a right angle or an obtuse angle with respect to the seeking direction. 9. The device of any of definitions 1-8 wherein the device has an entered configuration at which distal end of the vascular catheter is positioned within the cylindrically shaped target volume. 10. The device of any of definitions 1-9 wherein the medusa wire group has a cross-sectional area less than or equal to a cross-sectional area of a 0.038 inch wire guide; the entered configuration includes at least one of the separate wires being bent about and in contact with the distal end of the vascular catheter; and the distal end direction of each of the at least one wires bent about the distal end of the vascular catheter is at an obtuse angle with respect to the seeking direction. 11. In another aspect, a method of accessing a branch passageway from a main passageway with a device comprising the steps of: positioning a vascular catheter of the device in the main passageway so that a seeking direction defined by a distal end of the vascular catheter points into the branch passageway; simultaneously sliding a medusa wire group, of the device, that includes at least three separate wires from within the vascular catheter to a seeking configuration in which a distal segment of each of the separate wires is spaced from the distal end of the vascular catheter, and a distal end direction defined be each of the separate wires is at an acute angle with respect the seeking direction; and changing the device to an access configuration in which the distal end segment of at least one of the separate wires is positioned within the branch passageway. 12. The method of definition 11 including sliding at least one of the separate wires with respect to an other one of the separate wires. 13. The method of any of definitions 11 or 12 including moving the distal end of the vascular catheter along a net wire direction that is an average of all the distal end directions. 14. The method of any of definitions 11-13 including bending at least one of the separate wires about and in contact with the distal end of the vascular catheter. 15. The method of any of definitions 11-14 including bending the at least one wire to orient the distal end direction at an obtuse angle with respect to the seeking direction. 16. The method of any of definitions 11-15 wherein at least one of the separate wires extends through a fenestration of a stent graft in the access configuration. 17. The method of any of definitions 11-16 wherein the main passageway is an aorta; and the branch passageway is a renal artery. 18. The method of any of definitions 11-17 including a step of exchanging a 0.038 inch wire guide for the medusa wire group in the vascular catheter.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A medical device comprising:
  a vascular catheter that terminates at a distal end that defines a seeking direction;
  a medusa wire group that includes at least three separate wires slidably received in, and extending a full length of, the vascular catheter;
  the device having a maneuvering configuration in which a distal end of each of the separate wires is completely positioned inside the vascular catheter;
  the device having a seeking configuration in which a distal segment of each of the separate wires is spaced from the distal end of the vascular catheter and freely movable with respect to each other, and a distal end direction defined by each of the separate wires being at an acute angle with respect the seeking direction defined by the vascular catheter;
  the device having an access configuration in which the distal end segment of at least one of the separate wires is positioned within a cylindrically shaped target volume that is outside of the vascular catheter, and the cylindrically shaped target volume is intersected by a line coincident with the seeking direction.

2. The device of claim 1 wherein the separate wires are fixed against relative movement with respect to each other along an axis of the vascular catheter and within the vascular catheter.

3. The device of claim 1 wherein the separate wires are slidable with respect to each other along an axis of the guide catheter and within the vascular catheter.

4. The device of claim 1 wherein the access configuration includes a majority of the distal end directions being at an acute angle with respect to an average distal end direction of the majority, and a minority of the distal end directions are at an obtuse angle with respect to the seeking direction.

5. The device of claim 1 wherein the access configuration includes a distal end of at least one of the separate wires positioned inside the vascular catheter.

6. The device of claim 1 wherein the medusa wire group has a cross-sectional area less than a cross-sectional area of a 0.038 inch wire guide.

7. The device of claim 1 wherein the access configuration includes at least one of the separate wires is bent about and in contact with the distal end of the vascular catheter.

8. The device of claim 7 wherein the distal end direction of each of the at least one wires bent about the distal end of the vascular catheter is at a right angle or an obtuse angle with respect to the seeking direction.

9. The device of claim 1 wherein the device has an entered configuration at which distal end of the vascular catheter is positioned within the cylindrically shaped target volume.

10. The device of claim 9 wherein the medusa wire group has a cross-sectional area less than or equal to a cross-sectional area of a 0.038 inch wire guide;
  the entered configuration includes at least one of the separate wires being bent about and in contact with the distal end of the vascular catheter; and the distal end direction of each of the at least one wires bent about the distal end of the vascular catheter is at an obtuse angle with respect to the seeking direction.

11. A method of accessing a branch passageway from a main passageway with a device that includes a vascular catheter that terminates at a distal end that defines a seeking direction; a medusa wire group that includes at least three separate wires slidably received in, and extending a full length of, the vascular catheter; the device having a maneuvering configuration in which a distal end of each of the separate wires is completely positioned inside the vascular catheter; the device having a seeking configuration in which a distal segment of each of the separate wires is spaced from the distal end of the vascular catheter and freely movable with respect to each other, and a distal end direction defined by each of the separate wires being at an acute angle with respect the seeking direction defined by the vascular catheter; the device having an access configuration in which the distal end segment of at least one of the separate wires is positioned within a cylindrically shaped target volume is outside of the vascular catheter, and the cylindrically shaped volume is intersected by a line coincident with the seeking direction, the method comprising the steps of:

positioning the vascular catheter of the device in the main passageway so that a the seeking direction defined by a distal end of the vascular catheter points into the branch passageway;

simultaneously sliding the medusa wire group, of the device, that includes at least three separate wires from within the vascular catheter to the seeking configuration in which the distal segment of each of the separate wires is spaced from the distal end of the vascular catheter, and the distal end direction defined be each of the separate wires is at an acute angle with respect the seeking direction;

changing the device to the access configuration in which the distal end segment of at least one of the separate wires is positioned within the branch passageway.

12. The method of claim 11 including sliding at least one of the separate wires with respect to an other one of the separate wires.

13. The method of claim 11 including moving the distal end of the vascular catheter along a net wire direction that is an average of all the distal end directions.

14. The method of claim 13 including bending at least one of the separate wires about and in contact with the distal end of the vascular catheter.

15. The method of claim 14 including bending the at least one wire to orient the distal end direction at an obtuse angle with respect to the seeking direction.

16. The method of claim 11 wherein at least one of the separate wires extends through a fenestration of a stent graft in the access configuration.

17. The method of claim 11 wherein the main passageway is an aorta; and the branch passageway is a renal artery.

18. The method of claim 11 including a step of exchanging a 0.038 inch wire guide for the medusa wire group in the vascular catheter.

\* \* \* \* \*